United States Patent
Murray et al.

(10) Patent No.: US 9,675,367 B2
(45) Date of Patent: Jun. 13, 2017

(54) GUIDE TOOL FOR RESECTION OF PATELLOFEMORAL JOINT

(75) Inventors: David Wycliffe Murray, Oxford (GB); Christopher Alexander Dodd, Oxford (GB); Russell Lloyd, Wiltshire (GB); Duncan Andrew Ridley, Bristol (GB); William Keith Thomas, Chippenham (GB)

(73) Assignee: BIOMET UK HEALTHCARE LIMITED (GB)

( * ) Notice: Subject to any disclaimer, the term of this patent is extended or adjusted under 35 U.S.C. 154(b) by 915 days.

(21) Appl. No.: 14/005,343

(22) PCT Filed: Mar. 16, 2012

(86) PCT No.: PCT/GB2012/050583
§ 371 (c)(1),
(2), (4) Date: Nov. 20, 2013

(87) PCT Pub. No.: WO2012/123758
PCT Pub. Date: Sep. 20, 2012

(65) Prior Publication Data
US 2014/0074100 A1    Mar. 13, 2014

(30) Foreign Application Priority Data
Mar. 17, 2011   (GB) .................................. 1104510.1

(51) Int. Cl.
A61B 17/17    (2006.01)
A61B 17/15    (2006.01)
A61F 2/38     (2006.01)

(52) U.S. Cl.
CPC ........ *A61B 17/1764* (2013.01); *A61B 17/155* (2013.01); *A61F 2/3877* (2013.01)

(58) Field of Classification Search
CPC .......................... A61B 17/155; A61B 17/1764
See application file for complete search history.

(56) References Cited

U.S. PATENT DOCUMENTS

| | | | |
|---|---|---|---|
| 4,721,104 A * | 1/1988 | Kaufman | A61B 17/1764 606/88 |
| 5,234,433 A | 8/1993 | Bert et al. | |
| 5,364,402 A | 11/1994 | Mumme et al. | |
| 5,486,180 A | 1/1996 | Dietz et al. | |
| 5,593,411 A | 1/1997 | Stalcup et al. | |
| 5,601,563 A | 2/1997 | Burke et al. | |
| 5,709,689 A * | 1/1998 | Ferrante | A61B 17/155 606/80 |

(Continued)

FOREIGN PATENT DOCUMENTS

| | | |
|---|---|---|
| EP | 0661023 A2 | 7/1995 |
| EP | 1084679 A2 | 3/2001 |

(Continued)

OTHER PUBLICATIONS

International Search Report and Written Opinion for PCT/GB2012/050583, mailed Jul. 30, 2012; ISA/EP.

(Continued)

*Primary Examiner* — Nicholas Woodall
(74) *Attorney, Agent, or Firm* — Schwegman Lundberg Woessner, P.A.

(57) ABSTRACT

A guide tool (100) for guiding resection of a bone piece, comprising a body (102), a burr guide opening (130) extending through the body (102) and defining a burr resection surface, and a saw guide opening (120) extending through the body (102) and defining a saw resection surface, the burr guide opening (130) and the saw guide opening (120) being aligned such that the burr resection surface and the saw resection surface intersect, defining a bone piece resection surface.

25 Claims, 13 Drawing Sheets

(56) References Cited

U.S. PATENT DOCUMENTS

| | | | |
|---|---|---|---|
| 5,860,981 | A | 1/1999 | Bertin et al. |
| 6,056,754 | A | 5/2000 | Haines et al. |
| 6,554,838 | B2 * | 4/2003 | McGovern ......... A61B 17/1764 606/87 |
| 6,916,324 | B2 * | 7/2005 | Sanford ............... A61B 17/155 606/87 |
| 2004/0153066 | A1 | 8/2004 | Coon et al. |
| 2004/0153087 | A1 * | 8/2004 | Sanford ............... A61B 17/155 606/88 |
| 2004/0260301 | A1 | 12/2004 | Lionberger et al. |
| 2005/0015153 | A1 | 1/2005 | Goble et al. |
| 2005/0192588 | A1 | 9/2005 | Garcia |
| 2006/0217734 | A1 | 9/2006 | Sanford et al. |
| 2007/0282451 | A1 * | 12/2007 | Metzger ............. A61B 17/1675 623/20.28 |
| 2008/0243127 | A1 | 10/2008 | Lang et al. |
| 2010/0036383 | A1 | 2/2010 | Major et al. |

FOREIGN PATENT DOCUMENTS

| | | |
|---|---|---|
| EP | 1374783 A1 | 1/2004 |
| EP | 1084679 B1 | 4/2006 |
| EP | 1374783 B1 | 4/2008 |
| EP | 2685915 A1 | 1/2016 |
| GB | 2489033 B | 5/2016 |
| JP | 2000501633 A | 2/2000 |
| JP | 2000505337 A | 5/2000 |
| JP | 2008522665 A | 7/2008 |
| JP | 2008540057 A | 11/2008 |
| JP | 11504532 A | 2/2011 |
| WO | WO-2006056754 A1 | 6/2006 |
| WO | WO-2006/135462 A2 | 12/2006 |
| WO | WO-2010/014808 A2 | 2/2010 |
| WO | WO-2012123758 A1 | 9/2012 |

OTHER PUBLICATIONS

Search Report of the Intellectual Property Office of the United Kingdom for priority application GB 1104510.1, mailed Jun. 30, 2011.

Patent Examination Report No. 2 issued Feb. 2, 2015 for Australia Patent Application No. 2012228032.
"Australian Application Serial No. 2012228032, First Examiner Report mailed Jul. 15, 2014", 3 pgs.
"Australian Application Serial No. 2012228032, Response filed Jun. 1, 2015 to Second Examiner Report mailed Feb. 2, 2015", 13 pgs.
"Australian Application Serial No. 2012228032, Response filed Dec. 19, 2014 to First Examiner Report mailed Jul. 15, 2014", 15 pgs.
"Canadian Application Serial No. 2,829,823, Notice of Allowance mailed Oct. 7, 2015", 1 pg.
"Canadian Application Serial No. 2,829,823, Office Action mailed Feb. 3, 2015", 5 pgs.
"Canadian Application Serial No. 2,829,823, Response filed Jul. 31, 2015 to Office Action mailed Feb. 3, 2015", 14 pgs.
"Canadian Application Serial No. 2,829,823, Voluntary Amendment filed Sep. 11, 2013", 5 pgs.
"European Application Serial No. 12713267.8, Communication Pursuant to Article 94(3) EPC mailed Feb. 10, 2016", 2 pgs.
"European Application Serial No. 12713267.8, Intention to Grant mailed Nov. 14, 2016", 33 pgs.
"European Application Serial No. 12713267.8, Response filed Jun. 14, 2016 to Communication Pursuant to Article 94(3) EPC mailed Feb. 10, 2016", 10 pgs.
"International Application Serial No. PCT/GB2012/050583, International Preliminary Report on Patentability mailed Sep. 26, 2013", 8 pgs.
"Japanese Application Serial No. 2013-558514, Notice of Allowance mailed Oct. 17, 2016", W/ English Translation of Claims, 5 pgs.
"Japanese Application Serial No. 2013-558514, Office Action mailed Dec. 14, 2015", W/ English Translation, 5 pgs.
"Japanese Application Serial No. 2013-558514, Response filed Jun. 13, 2016 to Office Action mailed Dec. 14, 2015", W/ English Translation of Claims, 7 pgs.
"United Kingdom Application Serial No. 1104510.1, Decision to Grant mailed Apr. 26, 2016", 2 pgs.
"United Kingdom Application Serial No. 1104510.1, Office Action mailed Feb. 5, 2016", 3 pgs.
"United Kingdom Application Serial No. 1104510.1, Response filed Apr. 5, 2016 to Office Action mailed Feb. 5, 2016", 10 pgs.

* cited by examiner

GUIDE TOOL FOR RESECTION OF PATELLOFEMORAL JOINT

CROSS-REFERENCE TO RELATED APPLICATIONS

This application is a 371 U. S. National Stage of International Application No. PCT/GB2012/050583, filed on Mar. 16, 2012 and published as WO 2012/123758 A1 on Sep. 20, 2012. This application claims priority to British Patent Application No. 1104510.1, filed on Mar. 17, 2011. The disclosures of the above applications are incorporated herein by reference in their entirety.

The present invention relates to a guide tool and particularly although not exclusively to a guide tool for guiding resection of the distal femur prior to implantation of a femoral resurfacing prosthesis for the patellofemoral joint.

BACKGROUND

Joint resurfacing operations require the removal or resection of outer layers of bone, some or all of which may be diseased or degraded, in order to allow the implantation of a resurfacing prosthesis. The resurfacing prosthesis includes a bone engaging surface, that contacts and may be cemented to the exposed bone surface, and a bearing surface, designed to articulate with an adjacent natural or artificial bearing surface. In order to ensure correct operation of the reconstructed joint, the bearing surface of the resurfacing prosthesis must be in the correct anatomical position relative to the adjacent structures. To promote stability of the reconstructed joint, it is important that the bone engaging surface of the implant matches closely the resected surface of bone onto which it will be secured. It is also desirable to achieve a smooth transition from prosthesis to bone surface at the edges of the implant. The smoothness of this transition is determined by the accuracy of the resection of the existing bone surface.

The patellofemoral joint is an example of a natural joint that may be resurfaced by implantation of a distal femoral prosthesis. Existing resurfacing operations for this joint require the free hand resection of the distal femur. Resection is normally accomplished by drawing around a template and using an osteotome or rasp to remove the bone. However, the bone engaging surface of a distal femoral prosthesis is a complex surface that varies in three dimensions. It is not possible to replicate such a surface using free hand tools, and hence such conventional methods do not enable a surgeon to achieve a perfect fit between resected bone surface and prosthetic implant. In addition, the free hand removal of a significant area of bone is highly surgically demanding.

SUMMARY OF INVENTION

According to the present invention, there is provided a guide tool for guiding resection of a bone piece, comprising a body, a burr guide opening extending through the body and defining a burr resection surface, and a saw guide opening extending through the body and defining a saw resection surface, the burr guide opening and the saw guide opening being aligned such that the burr resection surface and the saw resection surface intersect, defining a bone piece resection surface.

It will be appreciated that for the purposes of this specification, a surface may be planar or undulating, and may form a closed loop. For example, a saw guide opening may define a planar surface along which a saw blade will pass and penetrate into bone. A burr guide opening may be somewhat larger, to allow for the different mechanism of bone removal using a burr compared with using a saw. Thus a resection surface defined by a burr guide opening may comprise a closed loop about the region of bone that will be removed through the action of a burr guided by the opening. A bone piece resection surface may comprise a complex surface that varies in three dimensions and is formed of intersecting portions of burr and saw resection surfaces.

The burr resection surface and the saw resection surface may converge in a cutting direction, such that the bone piece resection surface is concave. A cutting direction will typically be into a bone surface, with burr and saw resection surfaces meeting at an internal angle of less than 180 degrees to form the concave bone piece resection surface.

The burr guide opening may define an undulating burr resection surface and may comprise a locating feature.

The locating feature may for example be a notch on one side or another of the burr guide opening. The locating feature may be positioned substantially centrally on the burr guide opening, and may be operable to align with an anatomical feature of a bone. For example, the locating feature may be operable to align with the femoral trochlea in preparation for resection as part of a resurfacing of the patellofemoral joint.

The body of the tool guide may comprise a plate, which may be operable in use to rest on a resected bone surface. The plate may for example be an anterior plate operable to rest on a resected anterior surface of a distal femur.

The saw guide opening may extend through the plate and may be angled with respect to the plane of the plate.

An edge of the plate may be shaped to match the corresponding edge of a prosthesis to be implanted following resection of the bone piece. In this manner, the edge may function as a secondary locating feature, enabling visualisation of where the eventually implanted prosthesis will rest on a bone surface.

The body further may comprise a shelf, which may project from an edge of the anterior plate. The shelf may be integrally formed with the anterior plate.

The shelf may be a condylar shelf.

The shelf may be angled with respect to the plate, for example to approximate the curve of a distal femur.

The shelf may be curved across a lateral medial axis, for example to present a convex bone side face that may mirror to some extent the natural concavity of the inter condylar notch of a distal femur. The shelf may present an opposed concave face to a cutting instrument.

The burr guide opening may extend through the shelf.

The guide tool may further comprise at least one lug which may project from a bone engaging face of the shelf. The guide tool may comprise at least two lugs which may be dimensioned to provide a controlled stand off of the shelf from a bone surface. The lugs may provide a constant stand off from a bone surface. The lugs may be located on a region of the shelf that is remote from the junction with the plate.

The body may further comprise a window opening through the body and carrying a locating feature thereon. The window may be located for example on the lateral or medial side of the tool, for example on the plate or at a joining region between the plate and the shelf. The locating feature may be a notch or pair of aligned notches on opposed edges of the window. The notch or notches may correspond to the lateral or medial edge of the prosthesis to be implanted following resection of the bone piece. In this manner the window and notch or notches may serve as another location feature, enabling visualisation of where the eventually implanted prosthesis will rest on a bone surface.

The guide tool may further comprise an additional saw guide opening defining an additional saw resection surface that intersects the burr resection surface. The additional saw resection surface may also intersect the saw resection surface.

In this manner, the two saw resection surfaces may define a valley, an end of which intersects the burr resection surface to form the bone piece resection surface.

The body may further comprise a plurality of fixation openings, which may be operable to receive fixation elements. Suitable fixation elements may for example comprise pins or bone screws.

At least one of the fixation openings may be located between the saw guide opening and the burr guide opening. In this manner, at least one point of fixation for the guide tool may be located on the bone piece that is to be resected with the assistance of the tool.

At least one of the fixation openings may be of greater diameter than the other fixation openings. The at least one fixation opening may also be of greater diameter than a stem portion of a corresponding fixation element, such that some play may be accommodated between the fixation element and the guide tool.

At least one of the fixation openings may be redundant. Such redundancy may afford a surgeon increased options for fixation location, so that if on correct alignment of the tool, one of the fixation openings is located over a bone void or diseased or degraded bone then another of the fixation openings can be used without compromising overall stability of the tool.

The guide tool may further comprise at least one drill guide opening and may for example comprise three drill guide openings.

The drill guide openings may be operable to guide drilling of peg holes for the prosthesis to be implanted following resection of the bone piece.

The guide tool may be for guiding resection of the distal femur in the region of the patellofemoral joint.

BRIEF DESCRIPTION OF DRAWINGS

For a better understanding of the present invention, and to show more clearly how it may be carried into effect, reference will now be made, by way of example, to the following drawings, in which.

DETAILED DESCRIPTION OF EMBODIMENTS

Figure 2:
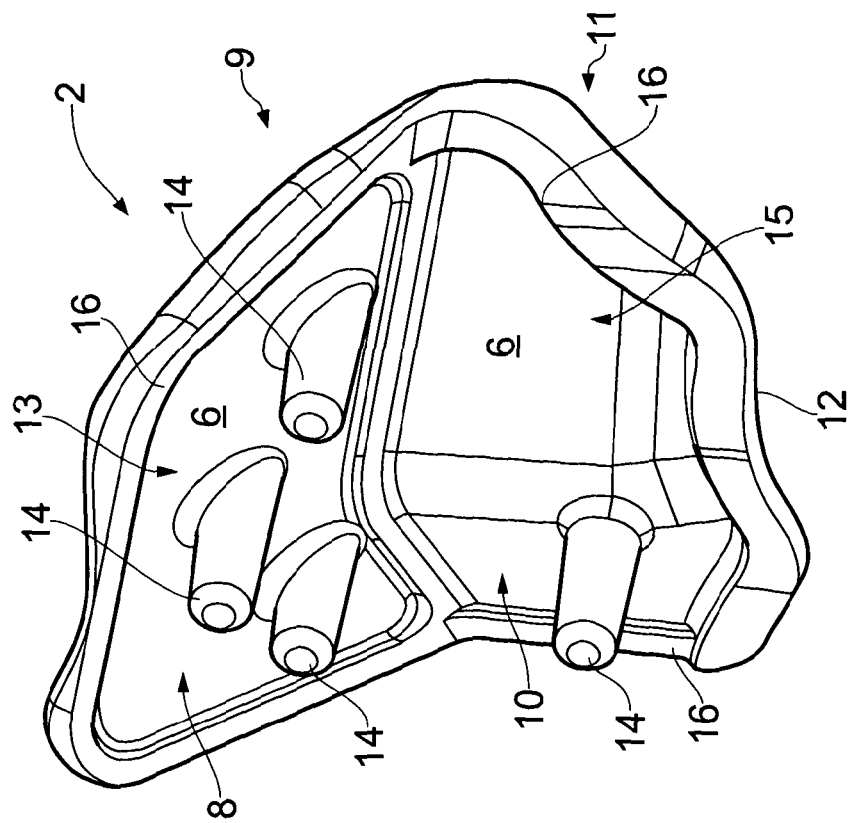
FIGS. 2 and 3 are alternative perspective views of the prosthesis of FIG. 1, showing a bone engaging surface.
Figure 1:
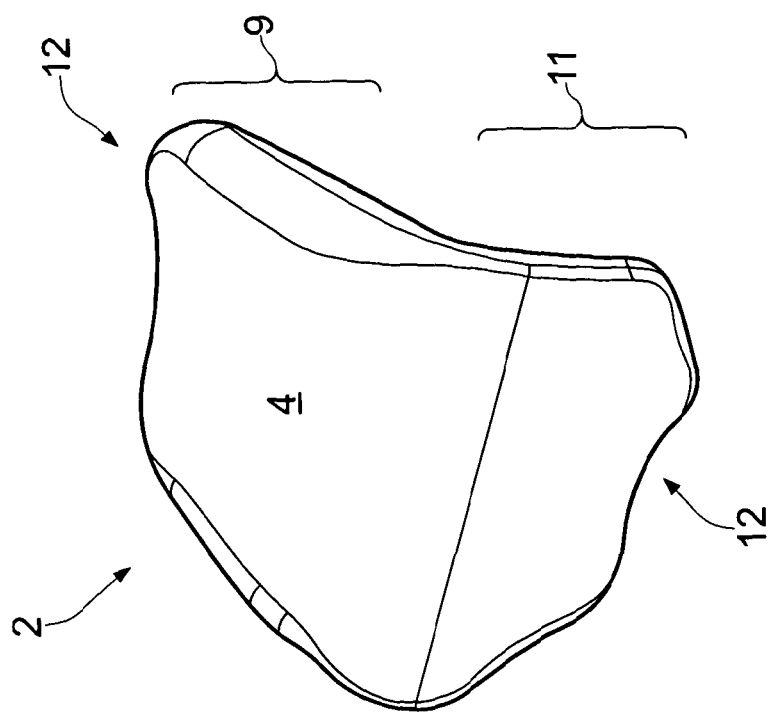
FIG. 1 is a perspective view of a femoral resurfacing prosthesis, showing an articulating surface.
Figure 3:
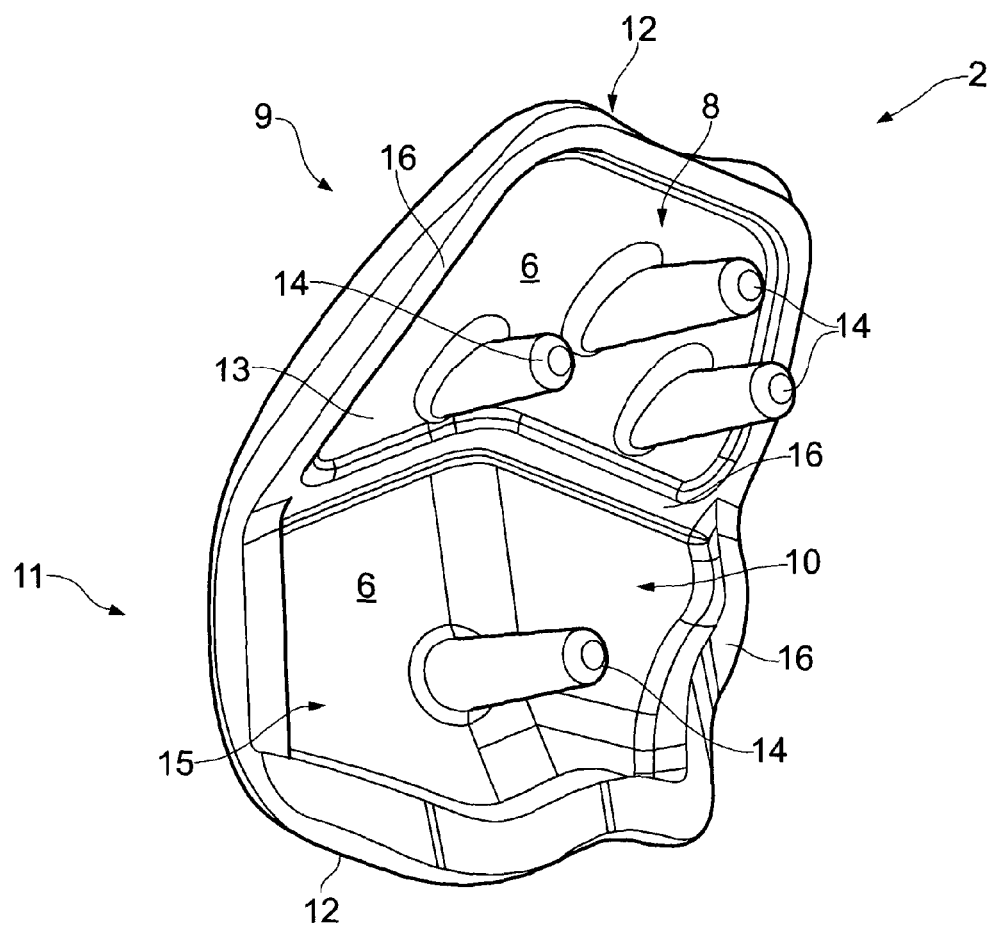

A femoral resurfacing prosthesis 2 for a patellofemoral joint is illustrated in FIGS. 1 to 3. The prosthesis 2 comprises an articulating surface 4 that is shaped to articulate with a patella resurfacing prosthesis or natural patella (not shown) and a bone engaging surface 6. The bone engaging surface is designed to rest adjacent a resected distal femoral surface and may be cemented in place. It will be appreciated that the bone engaging surface 6 is a relatively complex surface, varying in three dimensions. The surface 6 comprises a first substantially planar part 8 and a second substantially "V" shaped part 10, the two parts 8, 10 of the bone engaging surface 6 corresponding to anterior 9, and posterior 11 regions of the prosthesis 2 respectively. Each part 8, 10 of the bone engaging surface may be slightly recessed, with a protruding border 16 around its periphery. The recessed surfaces 8, 10 and borders 16 define two shallow recesses 13, 15 within which bone cement may be loaded for secure fixation of the prosthesis. The periphery 12 of the prosthesis 2 follows an undulating path, particularly in the region of the second part 10 of the bone engaging surface 6. Four fixation pegs 14 protrude from the bone engaging surface 6 to be received in corresponding holes drilled in the bone surface on which the prosthesis is to be mounted. Other embodiments of prosthesis (not shown) may comprise a different number of fixation pegs 14. For example a smaller femoral resurfacing prosthesis 2, designed for smaller patients, may comprise only three fixation pegs 14.

Figure 4:
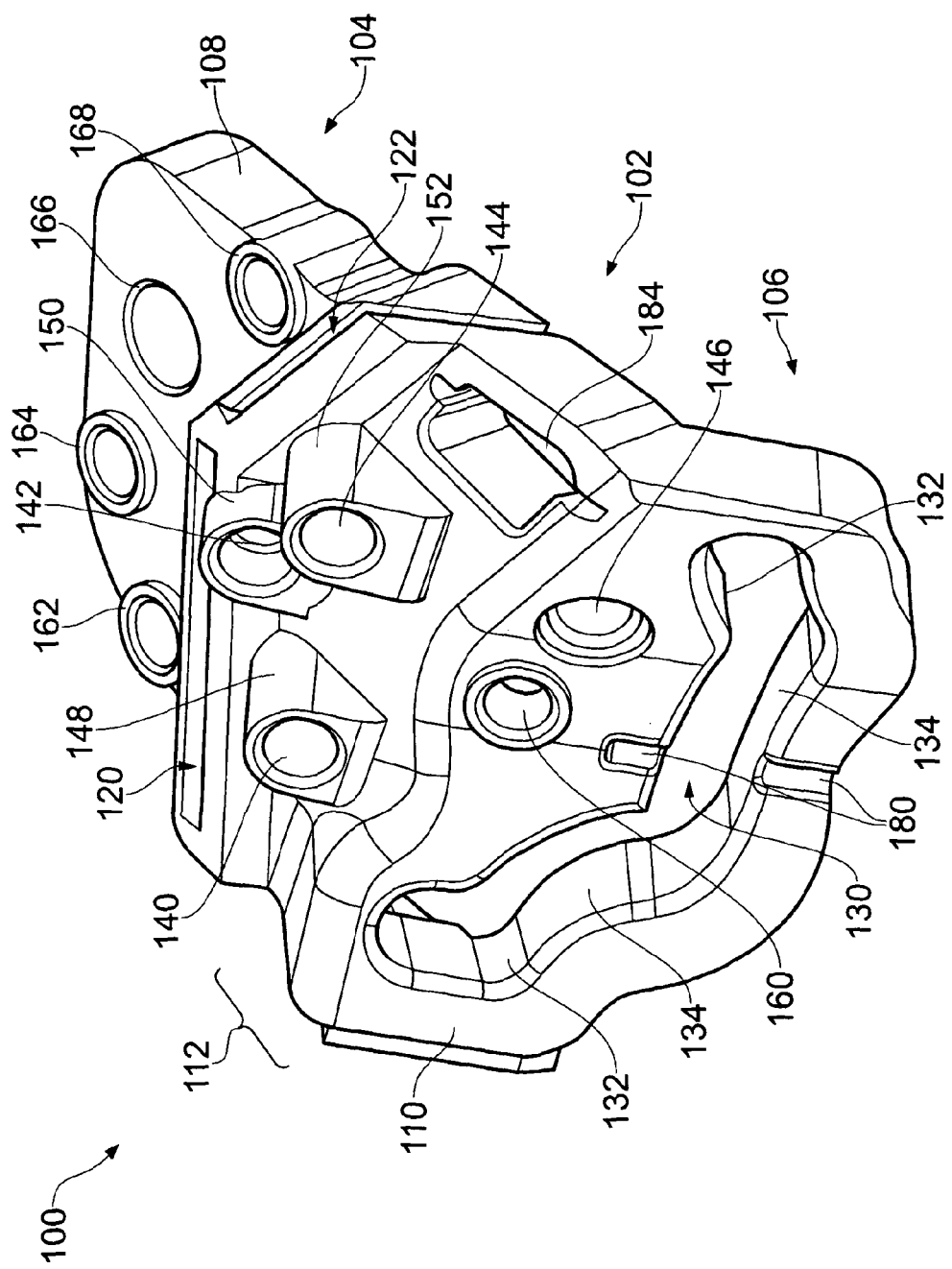
FIG. 4 is a perspective view of a guide tool.
Figure 5:
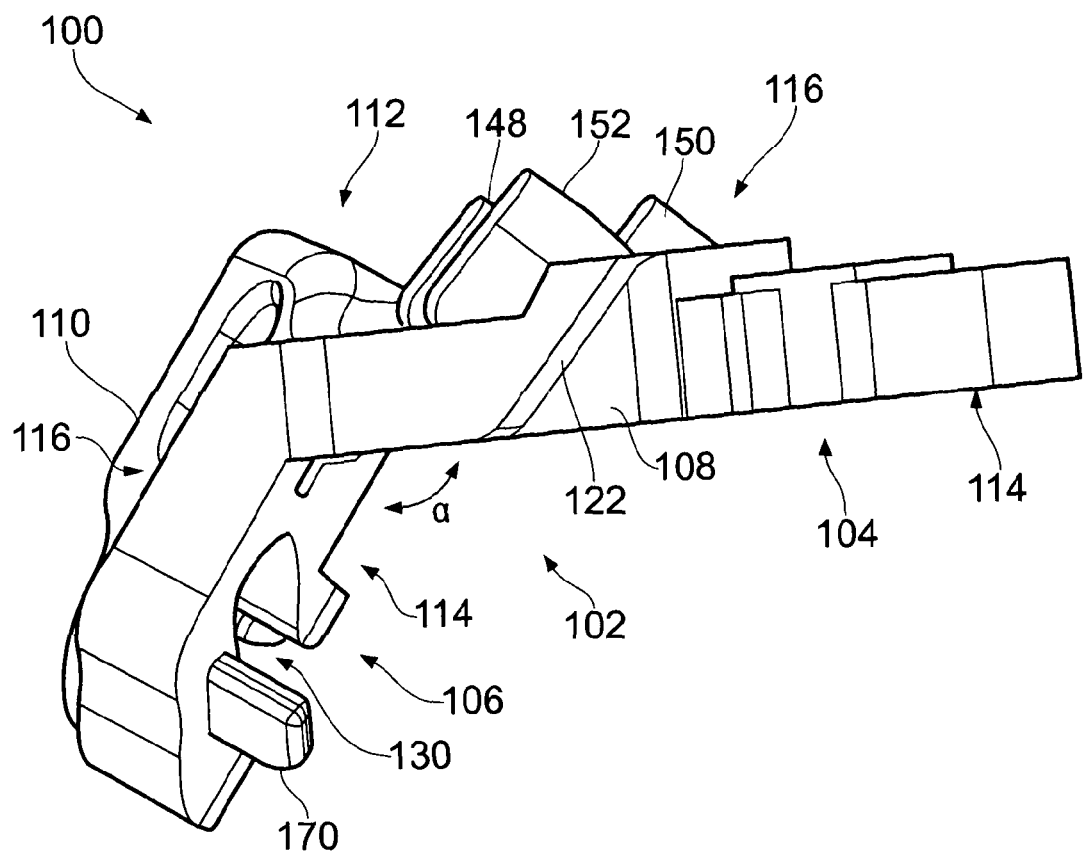
FIG. 5 is a side view of the guide tool of FIG. 4.
Figure 6:
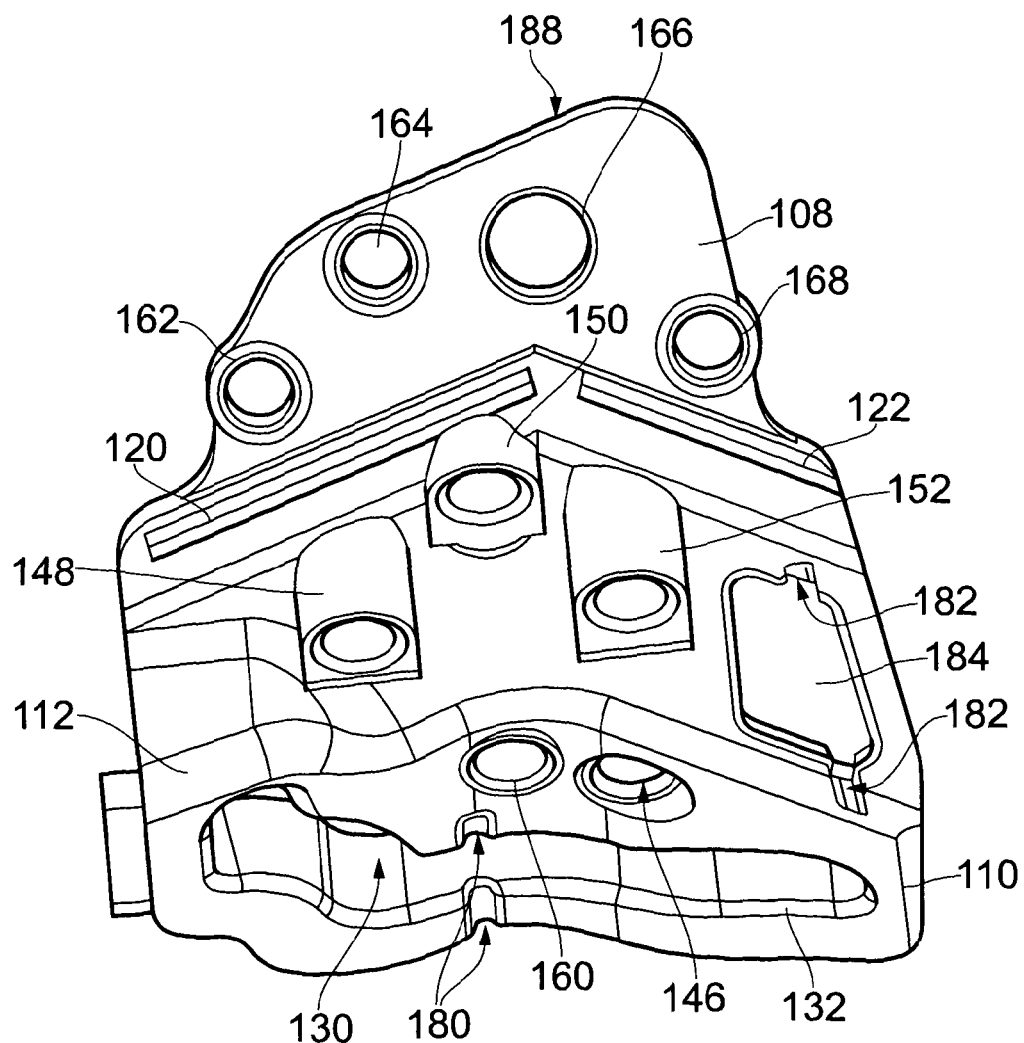
FIG. 6 is a top view of the guide tool of FIG. 4.
Figure 7:
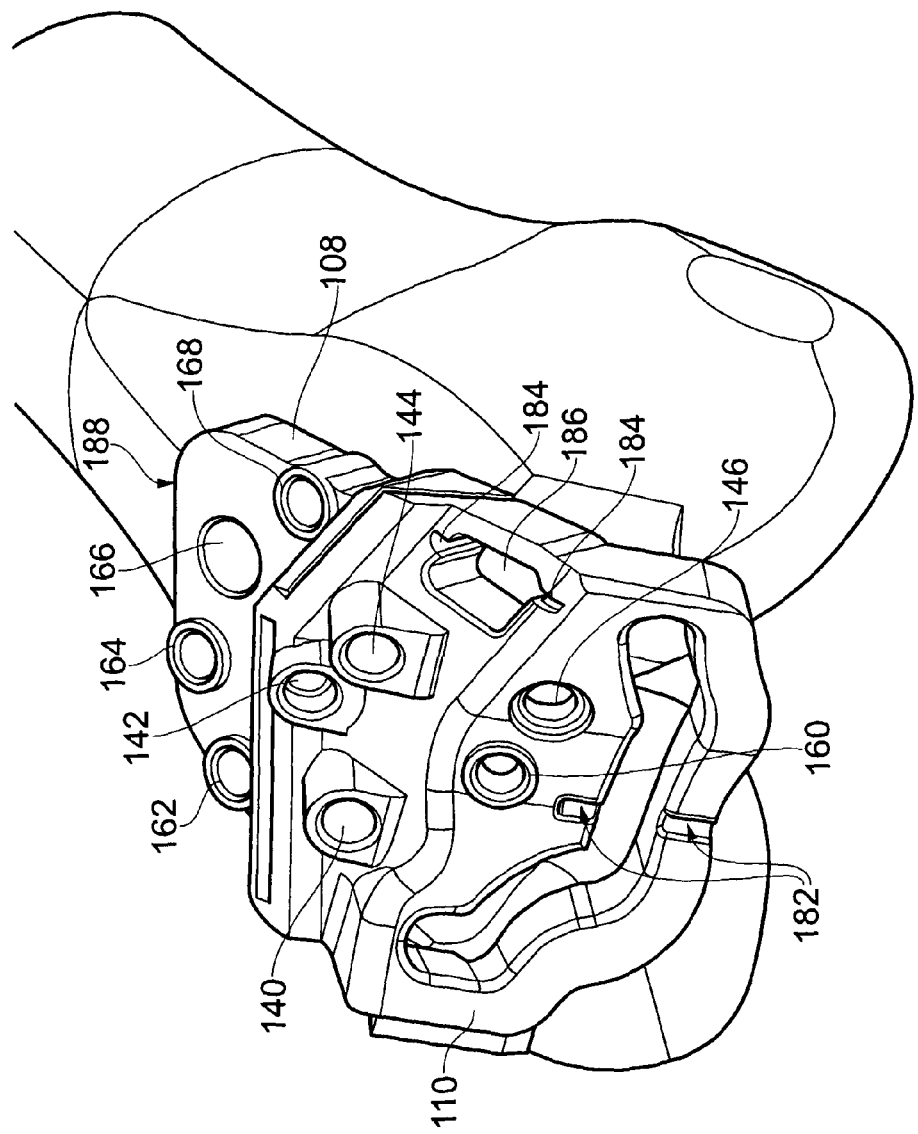
FIG. 7 is a perspective view of the guide tool of FIG. 4 in place on a distal portion of a femur.

With reference to FIGS. 4 to 6, a guide tool 100, suitable for guiding resection of a distal femur, comprises a body 102 having first and second parts 104, 106. The first part 104 comprises an anterior plate 108, which extends in a first plane. The second part 106 comprises a condylar shelf 110, which is integrally formed with the anterior plate 108 and projects out of the plane of the anterior plate 108 at an angle α that varies across the width of the tool 100. The anterior plate 108 and condylar shelf 110 meet at a joining region 112. The guide tool 100 comprises a bone side face 114 and a cutting side face 116. In the case of the anterior plate 108, the bone side face is a bone engaging face 114. At the joining region 112 of the tool, the bone side face ceases to be a bone engaging face, as explained in further detail below. The condylar shelf 110 is curved across a medial lateral axis, so as to present a concave cutting side face 116 and a convex bone side face 114. The convex bone side face 114 may substantially approximate the concavity of an intercondylar notch of a distal femur, adjacent to which the condylar shelf is adapted to rest.

The guide tool 100 comprises first and second saw guide openings 120, 122 extending through the anterior plate 108 of the tool 100. The saw guide openings 120, 122 each define a respective planar saw resection surface, along which a reciprocating saw (not shown) will travel when guided by the guide openings. Each of the saw guide openings 120, 122 is angled with respect to the anterior plate 108 so as to be approximately parallel to the corresponding region of the condylar shelf 110. The saw guide openings 120, 122 are thus also angled with respect to each other, such that the planar saw resection surfaces together define a valley extending away from the anterior plate 108. The saw guide openings 120, 122 may be closed at each side, as illustrated on the left of FIGS. 4 and 6, or may be open at one side, as illustrated on the right of FIGS. 4 and 6.

The guide tool 100 also comprises a burr guide opening 130 extending through the condylar shelf 110. The burr guide opening 130 follows an undulating path across the condylar shelf from the medial to the lateral side. The opening is defined by a closed loop periphery 132, which periphery defines a burr resection surface, extending away from the condylar shelf, substantially perpendicular to the shelf. A lower, or posterior region 134 of this periphery 132 substantially corresponds to the posterior periphery 12 of the prosthesis 2 which is to be implanted. In contrast to the saw guide openings 120, 122, which guide cutting of a bone region along a plane, the burr guide opening guides removal of an entire region of bone, this being the region bordered by the closed loop 132 of the burr resection surface.

Drill guide openings 140, 142, 144, 146 extend through the body 102 of the tool 100, and are operable to guide a substantially cylindrical drill bit along drilling axes. The drill guide openings are arranged in a group of three openings 140, 142, 144 that extend through the anterior plate 108 and a single opening that extends through the condylar shelf 110. The anterior plate drill openings 140, 142, 144 are defined by angled projections 148, 150, 152 that form supporting shoulders to the openings, providing added stability to a guided drill bit and defining the angled drilling axes. The condylar shelf drill guide opening 146 may also comprise a supporting shoulder (not shown). Each of the drill guide openings 140, 142, 144, 146 is located and angled to correspond to a respective one of the fixation pegs 14 of the femoral prosthesis 2. A guide tool 100 for use with a smaller femoral resurfacing prosthesis 2 having only three fixation pegs 14 may correspondingly comprise only three drill guide openings, opening 142 on the anterior plate 108 being omitted Fixation openings also extend through the body 102 of the drill guide 100, to enable the passage of fixation elements in the form of pins or screws (not shown). A first fixation opening 166 extends through the anterior plate 108 and is of larger diameter than the other fixation openings, for cooperation with a large headed nail, as described in further detail below. A second fixation opening 160 extends through the condylar shelf 110 close to a central region of the shelf 110 and between the burr guide opening 130 and the joining region 112 with the anterior plate 108. The remaining fixation openings 162, 164, 168 also extend through the anterior plate 108 and are of a similar diameter to the second fixation opening 160, dimensioned to accept an appropriate fixation element.

With particular reference to FIG. 5, two lugs 170, 172 (not shown) project from the bone facing surface 114 of the condylar shelf 110, substantially at right angles to the bone facing surface 114 of the condylar shelf 110. Free ends of the lugs 170, 172 are operable to engage a condylar bone surface and, when the tool 100 is in place on a distal femur, the lugs 170, 172 provide a controlled stand off from the condylar bone surface on which they rest. The lugs 170, 172 may be of differing lengths to accommodate the geometry of the adjacent condylar bone surface and place the guide tool 100 at a desired offset position from the condylar bone surface.

A plurality of positioning or locating features is incorporated into the tool 100. A notch 180 is formed in the cutting side face 116 of the condylar shelf 110, spanning the burr guide opening 130. The notch is located on the cutting side face of the condylar shelf so as to be operable for alignment with the centre of the femoral trochlea, as described below. A similar notch 182 is formed in the anterior plate 108, spanning a window 184 that opens through the anterior plate 108. The notch 184 is located so as to indicate the lateral outline of the prosthesis 2 that is to be implanted. The periphery 188 of the anterior plate is also shaped to match the periphery 12 of the anterior region 9 of the prosthesis, providing an indication of where the prosthesis 2 will rest once resection of the bone surface has been completed.

Use of the guide tool 100 will now be described with reference to FIGS. 7 to 14 and a femoral resurfacing procedure for the patellofemoral joint.

In a femoral resurfacing procedure, an incision must first be made and soft tissues retracted to give access to the joint. The patella may be everted or subluxed to allow access to the anterior and condylar surfaces of the distal femur.

The anterior femoral surface is resected to give a planar anterior bone surface. The guide tool 100 is then mounted on the distal femur, with the anterior plate 108 resting on the resected anterior femoral surface and the lugs 170, 172 resting against the surface of the femoral condyles. The angling of the condylar shelf 110 of the guide tool 100 enables the condylar shelf to follow approximately the curve of the distal femur from anterior surface to condylar surface. The curve of the condylar shelf 110 in the medial lateral direction substantially traces the curve of the inter condylar notch, allowing the lugs to rest against the condylar surfaces. Basic alignment is then performed to ensure the guide tool 100 is in approximately the right place. This process is a simplified version of the fine alignment that is to be conducted in a later process step and is described in detail below.

Once basic alignment has been completed, and the guide tool 100 is in approximately the correct position, a large headed nail (not shown) is inserted through the first fixation opening 166 and into the bone. It will be appreciated that the first fixation opening is of larger diameter, and is thus "oversized" with respect to the nail. The large head of the nail engages against the cutting side face 116 of the anterior plate and prevents movement of the plate 108, and hence the tool 100, away from the anterior bone surface. However, the shaft of the large headed nail is not closely received within the first fixation opening, meaning that some movement between the tool 100 and the large headed nail in the plane of the anterior bone surface is accommodated.

With the guide tool 100 held against the anterior bone surface, fine alignment of the tool is conducted using the lugs 170, 172 and the alignment features of the tool 100. Firstly, the position of the guide tool 100 is adjusted until the lugs 170, 172 are seated firmly against the distal condylar surfaces. This ensures a correct and substantially constant stand off from the condylar surface, which in turn ensures correct depth of cut through the burr guide opening, as discussed in more detail below. The alignment notch 182 on the cutting side face of the condylar shelf 110 is then aligned with the centre of the femoral trochlea. Finally, the peripheral profile 188 of the anterior plate 108 and the lateral notch 184 and window 186 are used to visualise the eventual location of the implanted prosthesis and minor adjustment may be made with reference to the surrounding bone features.

With the guide tool correctly aligned, a nail or bone screw (not shown) is inserted through the second fixation opening 160 on the condylar shelf 110 and into the bone beneath. The head of the nail or screw engages on the cutting side face of the condylar shelf 110 and pushes the guide tool 100 firmly against the femoral condyles. It may be preferable to use a nail through the second fixation opening 160 to provide positional location. Two bone screws (not shown) are then inserted through any two of the three remaining fixation openings 162, 164, 168 on the anterior plate 108. In certain embodiments, the bone screws may be disposable. The additional two screws provide secure fixation and avoid any potential loosening of the guide during subsequent cutting steps. Using only two of the remaining three fixation openings ensures some redundancy in the provision of fixation openings, providing additional surgical option should one of the fixation openings be located above a bone void or above damaged or otherwise degraded bone tissue. The surgeon can select the most promising two fixation sites for the two remaining nails or bone screws. While an exemplary mode of fixation has been described with reference to nails or screws extending through particular fixation openings, it will be appreciated that a surgeon may select the most appropriate fixation element for a fixation opening during a surgical procedure.

Figure 8:
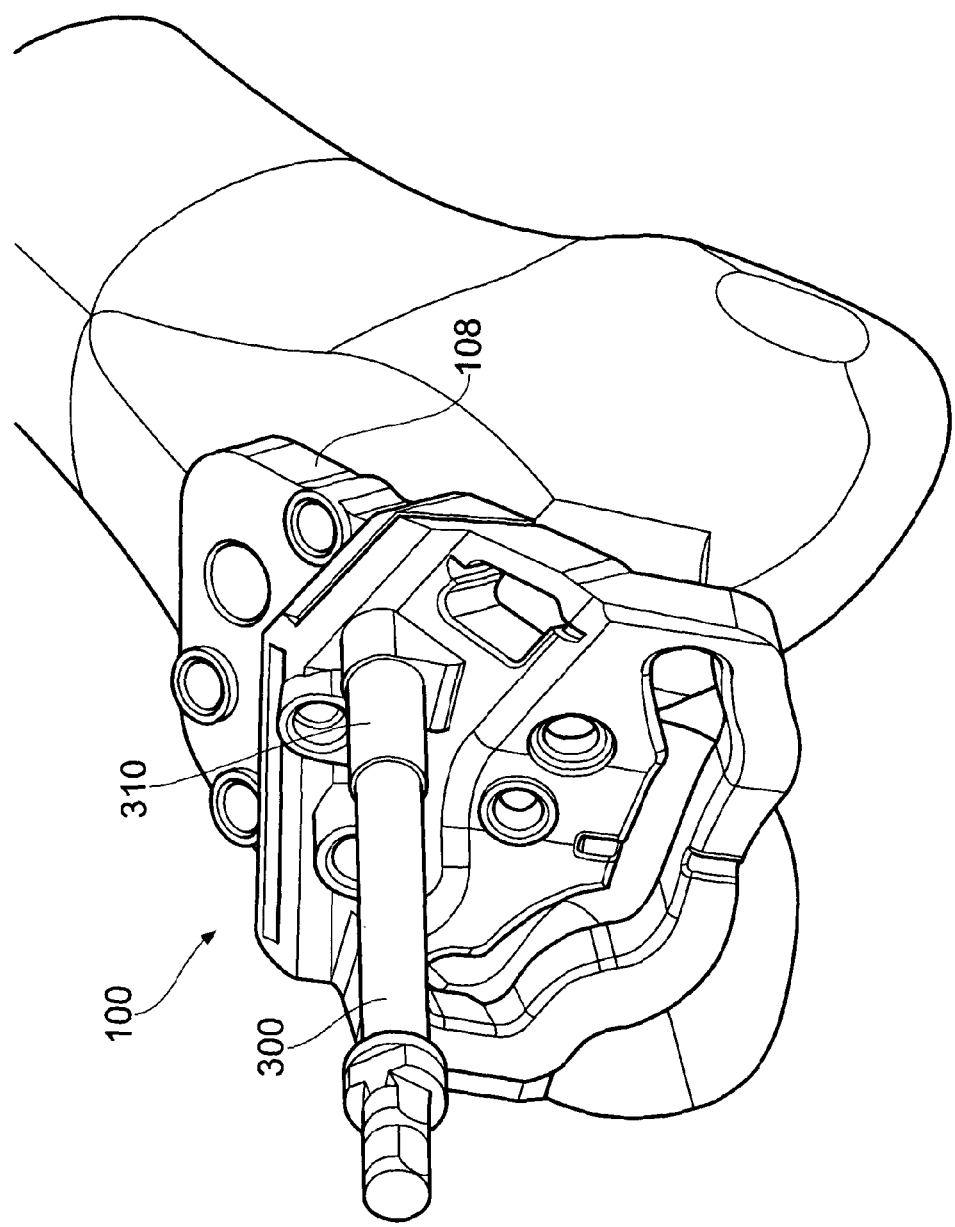
FIG. 8 is a perspective view of a drilling operation.

With the guide tool 100 securely fixed in place on the distal femur, the prosthesis peg holes are drilled through the drill guide openings 140, 142, 144, 146, as shown in FIG. 8. A standard surgical drill 300 may be used and a depth stop 310 can be employed to ensure the holes are drilled to the correct depth. The orientation of the drill guide openings through the body 102 of the guide tool 100, together with the supporting shoulders 148, 150, 152, ensures that the peg holes are drilled at the correct angle to receive the prosthesis fixation pegs 14. As described above, in the case of a guide tool for a smaller prosthesis, only three peg holes may be drilled through the three available drill guide openings.

In one embodiment, dummy pegs may then be inserted into the drilled peg holes, to engage both the drilled bone and the guide tool 100. The dummy pegs may provide an additional layer of fixation and stability during the process of conducting the burr cut.

Figure 9:
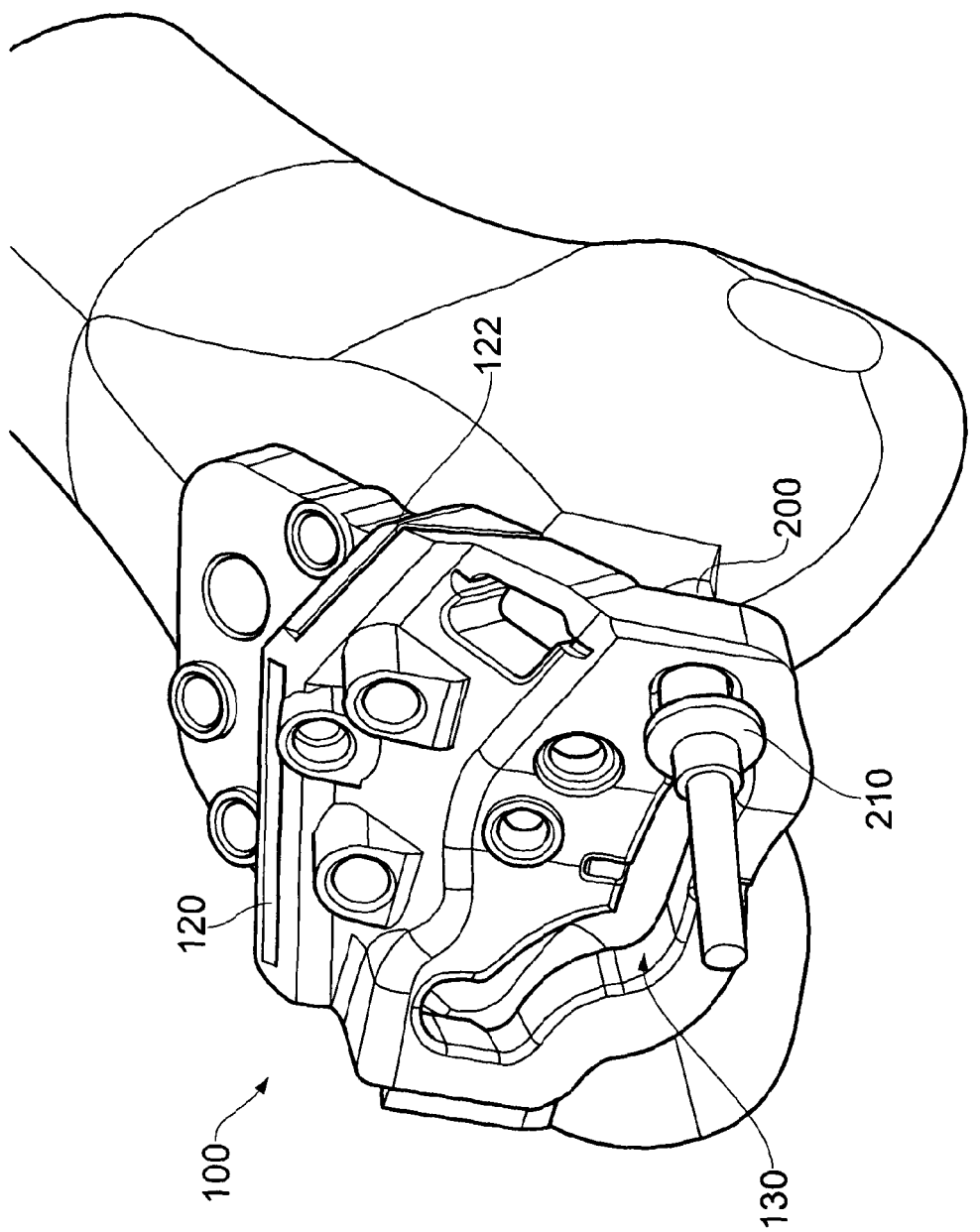
FIG. 9 is a perspective view of a burr cutting operation.

A burr cut is then made through the burr guide opening, using a rotating burr 200 and bearing 210 having a follower surface, as illustrated in FIG. 9. The length of the burr 200, from the follower surface of the bearing 210 to the end of the rotary burr, is selected to cooperate with the guide tool 100 and to be appropriate for the femoral prosthesis to be implanted 2. Thus, a profile cut is formed in the bone surface that is of precisely the correct depth to receive the femoral prosthesis 2 and to form a smooth transition form the articulating surface 4 of the prosthesis 2 to the surface of the remaining bone. The cooperation between the lugs 170, 172 of the guide tool 100, the thickness of the condylar shelf, and the rotary burr 200 and bearing 210 determines the depth of cut that is performed. The burr guide opening 130 directs the burr 200 in removing a region of bone tissue the posterior border of which precisely matches the periphery 12 of the posterior region 11 of the femoral prosthesis 2.

Figure 10:
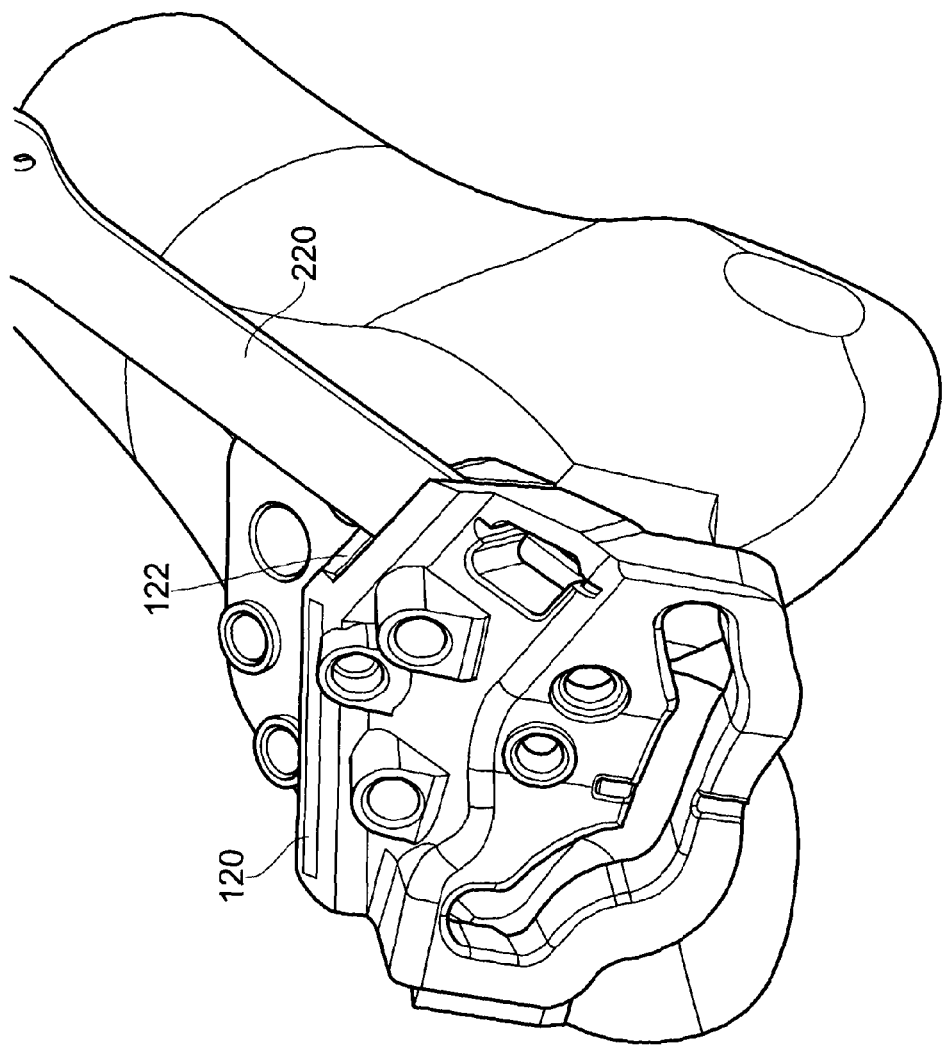
FIGS. 10 to 12 are perspective views of saw cutting operations.
Figure 11:
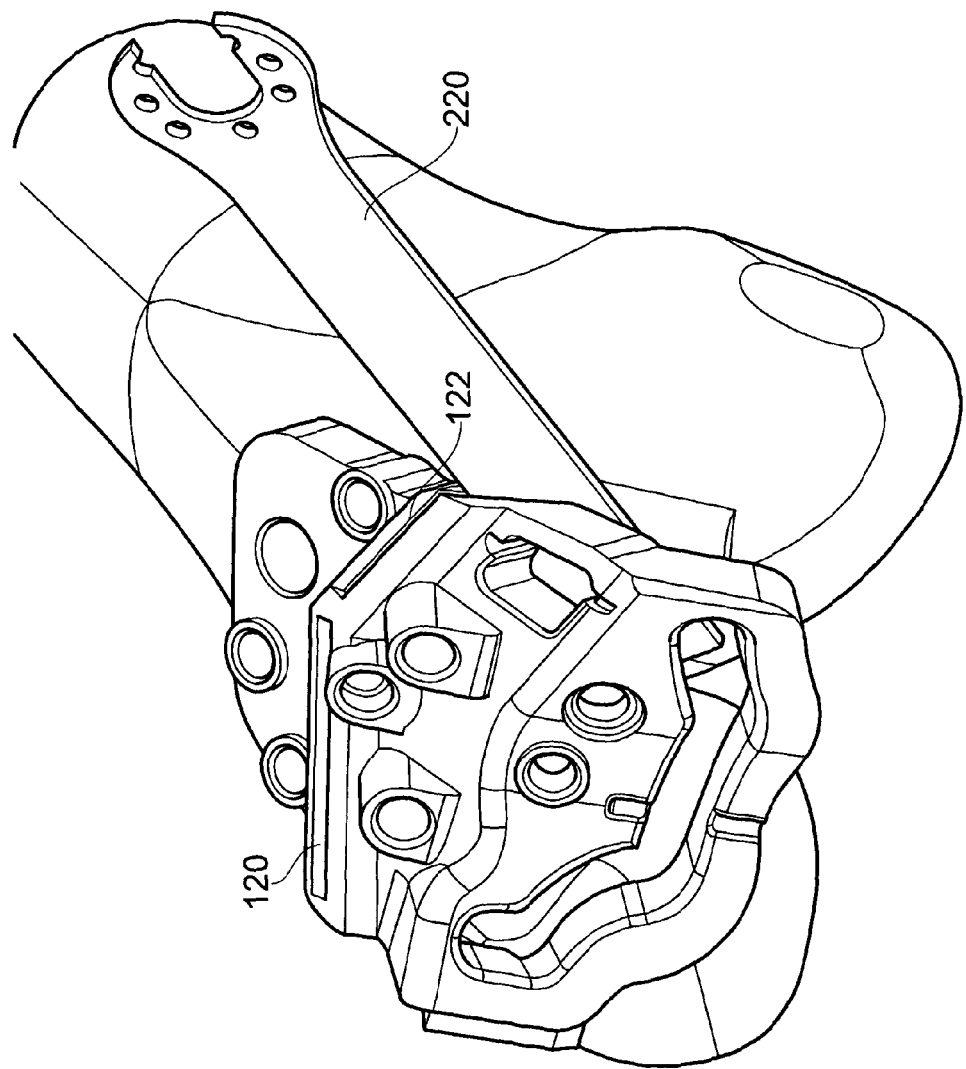
Figure 12:
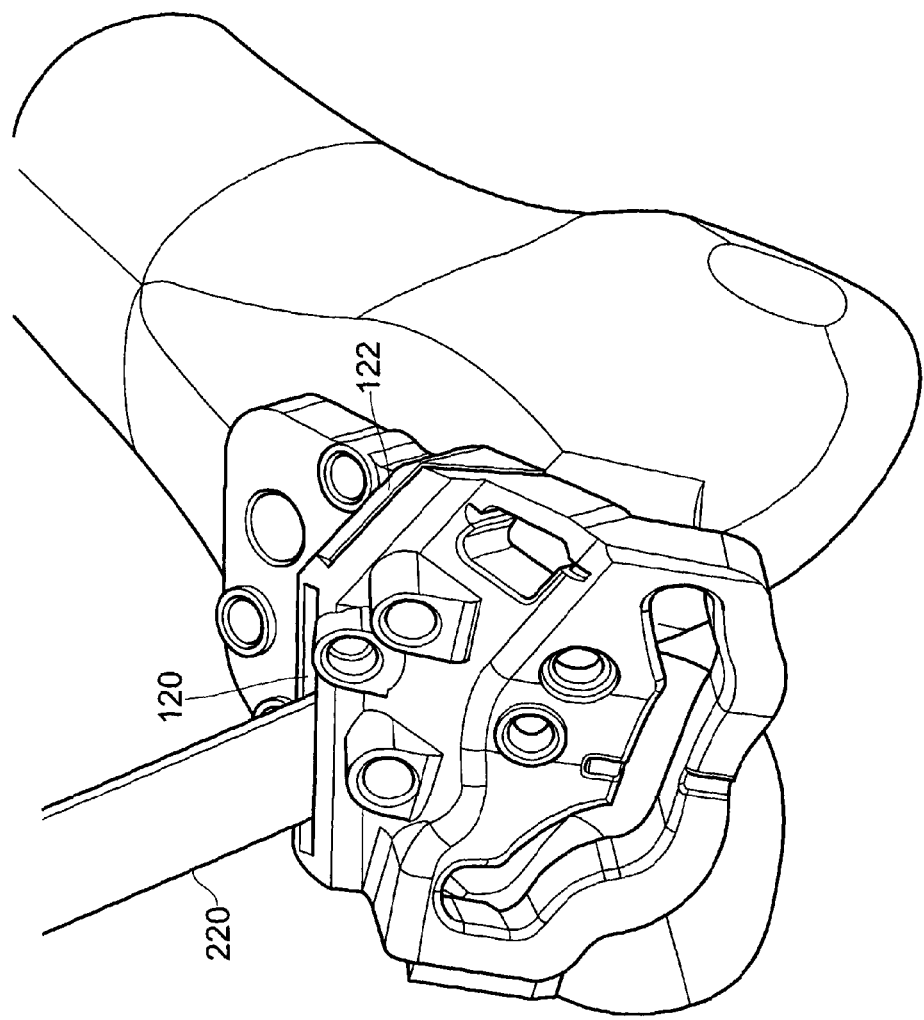
Figure 13:
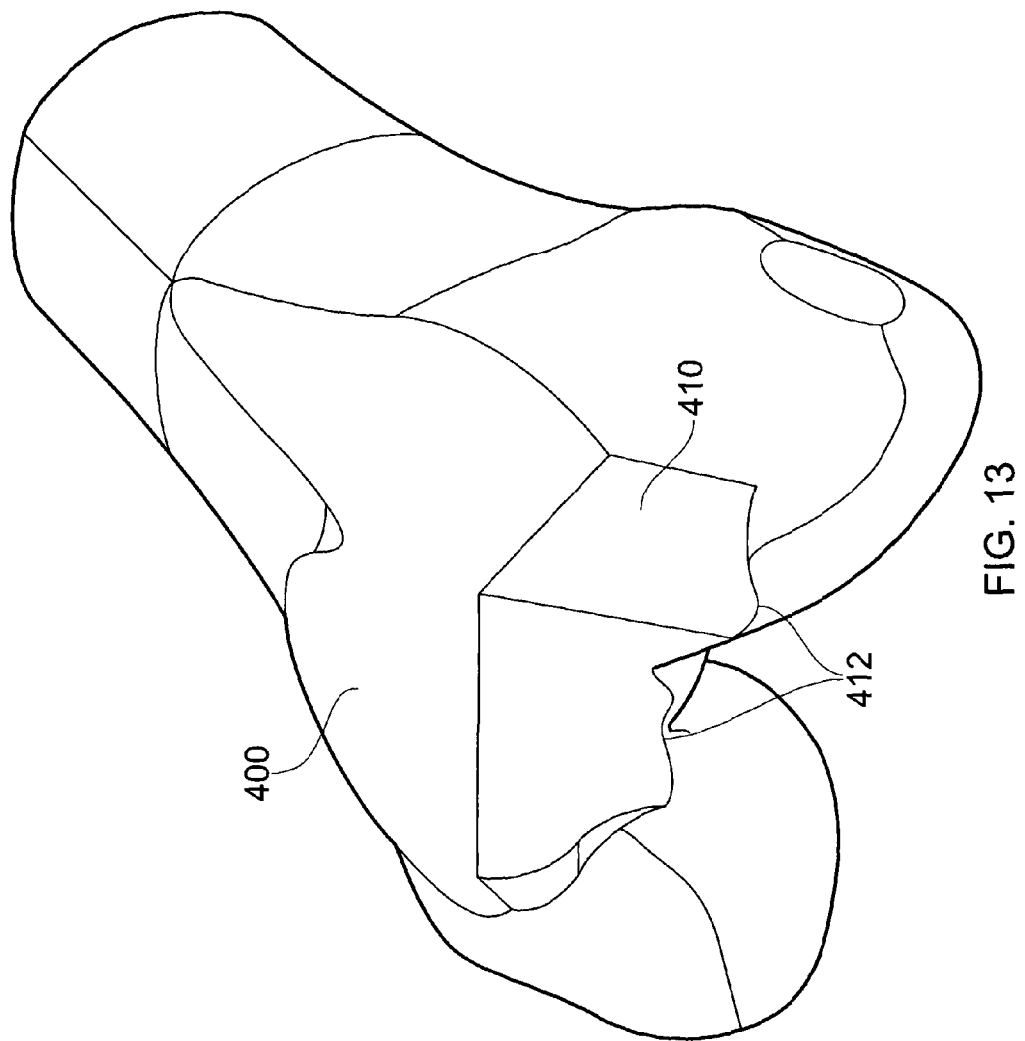
FIG. 13 is a perspective view of a resected distal femur.
Figure 14:
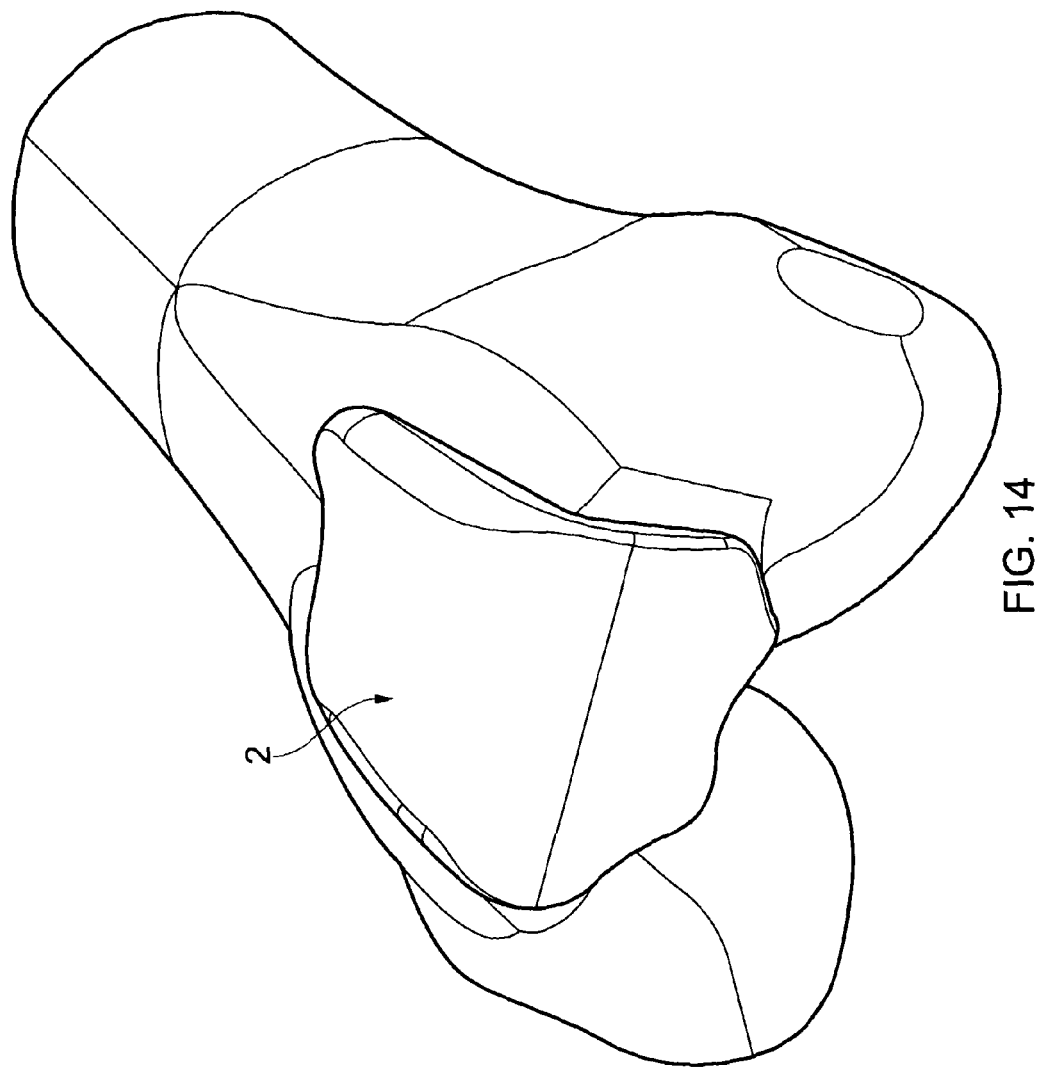
FIG. 14 shows the resected distal femur of FIG. 13 with the prosthesis of FIGS. 1 to 3 in place on the resected bone surface.

Following the burr cut, two saw cuts are made through the two saw guide openings 120, 122, as illustrated in FIGS. 10 to 12. A reciprocating saw 220 is inserted into first one and then the other of the saw guide openings 120, 122, to cut the bone tissue along the planar saw resection surfaces defined by the saw guide openings. In this manner, the guide tool 100 guides resection of a valley shaped bone piece starting at the anterior bone surface and intersecting the previously made burr cut. As the saw blade cuts through the last bone fibres and enters the burr cut, the sudden lack of resistance should be recognisable to the surgeon and signal that the saw blade should be retracted. However, it may be desirable to insert a stop into the burr cut, to prevent over cutting of the bone. The stop (not shown) may be a shaped, hand held metallic plate that closely matches the bottom or posterior profile of the burr cut. The stop may be held in place to prevent the reciprocating saw blade from penetrating into the bone tissue posterior to the burr cut.

It may be necessary to remove the nail or screw from the second fixation opening 160 prior to commencing the saw cuts, as the presence of a nail or screw extending through the second fixation opening 160 into the bone may interfere with passage of the saw blade.

With the saw cuts complete, an entire bone piece has been resected from the distal femur. The guide tool 100 is then detached from the anterior bone surface and removed, together with the resected bone piece. The resulting resected bone surface, illustrated in FIG. 13, comprises the planar anterior femoral bone 400 and a valley shaped recess 410 in the region of the trochlea that terminates at an undulating posterior profile 412. The resected bone surface is a precise match for the femoral resurfacing prosthesis 2, which can be seen in the implanted position in FIG. 14. The prosthesis 2 sits on the resected bone surface, the profiles of the bone and prosthesis 2 closely matching. The fixation pegs 14 are closely received in the drilled peg holes and the peripheral borders 16 of the two bone engaging regions are seated closely on the resected bone surface. The shallow bone cement recesses 13, 15 hold the bone cement that provides permanent fixation for the prosthesis.

It will be appreciated that while a particular embodiment of guide tool 100 has been described with reference to a patellofemoral resurfacing procedure, the present invention may be employed to provide a guide tool suitable for resecting a range of different bone surface portions as part of a number of resurfacing and other orthopaedic procedures.

It will also be appreciated that the guide tool of the present invention is a single piece; one integrally formed tool that incorporates within it features to allow for alignment of the tool 100 relative to the surrounding bone structure, fixation of the tool 100 to the bone, resection of a bone piece along a complex three dimensional surface, and drilling of implant peg holes.

No additional alignment, fixation or template tool is required to operate in conjunction with the tool of the present invention. The tool thus replaces known instrumentation kits of the prior art, that may require multiple fixations and alignments in order to complete different steps in a resection procedure, with a single apparatus. According to the present invention, all the cuts required to resect a complex bone surface can be performed using the same tool, with no requirement for intermediate alignment or fixation steps. In addition, implant peg holes can also be drilled through the same tool, again with no need to replace or realign the tool, nor for any additional or subsidiary guide tools to be attached.

It is an advantage of the present invention that all of the steps required for preparation of a bone surface to accept an implant can be conducted through the same tool following a single alignment and fixation procedure. The tool of the present invention thus greatly simplifies the preparation of a resected bone surface. With particular reference to the resurfacing of the femoral portion of the patellofemoral joint, the tool of the present invention imparts accuracy, efficiency and repeatability to a procedure that is conventionally carried out free hand and by eye in a time consuming and highly inaccurate manner.

The invention claimed is:

1. A guide tool for guiding resection of a bone piece, comprising:
    a body, a burr guide opening extending through the body and defining a burr resection surface, wherein the burr guide opening is defined by an undulating periphery, and a saw guide opening extending through the body and defining a saw resection surface, the burr guide opening and the saw guide opening being aligned such that the burr resection surface and the saw resection surface intersect, defining a bone piece resection surface.

2. The guide tool as claimed in claim 1, wherein the burr resection surface and the saw resection surface converge in a cutting direction, such that the bone piece resection surface is concave.

3. The guide tool as claimed in claim 1, wherein the burr guide opening comprises a locating feature.

4. The guide tool as claimed in claim 3, wherein the locating feature is positioned substantially centrally on the burr guide opening, and is operable to align with an anatomical feature of a bone.

5. The guide tool as claimed in claim 1, wherein the body comprises a plate, operable in use to rest on a resected bone surface.

6. The guide tool as claimed in claim 5, wherein the saw guide opening extends through the plate.

7. The guide tool as claimed in claim 5, wherein an edge of the plate is shaped to match the corresponding edge of a prosthesis to be implanted following resection of the bone piece.

8. The guide tool as claimed in claim 5, wherein the body further 35 comprises a shelf, projecting from an edge of the plate.

9. The guide tool as claimed in claim 8, wherein the shelf is angled with respect to the plate.

10. The guide tool as claimed in claim 8, wherein the shelf is curved across a lateral medial axis.

11. The guide tool as claimed in claim 8, wherein the burr guide opening extends through the shelf.

12. The guide tool as claimed in claim 8, further comprising at least one lug projecting from a bone side face of the shelf.

13. The guide tool as claimed in claim 1, wherein the body further comprises a window opening through the body and carrying a locating feature thereon.

14. The guide tool as claimed in claim 1, further comprising an additional saw guide opening defining an additional saw resection surface that intersects the burr resection surface, wherein the additional saw resection surface also intersects the saw resection surface.

15. The guide tool as claimed in claim 1, wherein the body further comprises a plurality of fixation openings, operable to receive fixation elements.

16. The guide tool as claimed in claim 15, wherein at least one of the fixation openings is located between the saw guide opening and the burr guide opening.

17. The guide tool as claimed in claim 15, wherein at least one of the fixation openings is of greater diameter than the other fixation openings.

18. The guide tool as claimed in claim 15, wherein at least one of the fixation openings is redundant.

19. The guide tool as claimed in claim 1, further comprising at least one drill guide opening.

20. The guide tool as claimed in claim 19, wherein the drill guide openings are operable to guide drilling of peg holes for a prosthesis to be implanted following resection of the bone piece.

21. The guide tool as claimed in claim 1, wherein the guide tool is for guiding resection of the distal femur in the region of the patellofemoral joint.

22. A guide tool for resecting a bone, comprising:
a body having a bone facing side, a burr guide opening extending through the body in a first direction and defining a burr resection plane, and a saw guide opening extending in a second direction through the body and defining a saw resection plane, the burr resection plane and the saw resection plane intersecting on the bone facing side of the body, wherein the burr guide opening is defined by an undulating periphery.

23. The guide tool as claimed in claim 22, wherein the burr resection plane and the saw resection plane intersect within an area defined by the bone.

24. The guide tool as claimed in claim 22, wherein the burr resection plane and the saw resection plane intersect at a mean distance from the bone facing side of the body of between about 5 mm and about 40 mm.

25. The guide tool as claimed in claim 22, wherein the burr resection plane and the saw resection plane intersect at a mean distance from the bone facing side of the body of between about 5 mm and about 30 mm.

* * * * *